(12) United States Patent
Al-Qaisi et al.

(10) Patent No.: US 11,490,804 B2
(45) Date of Patent: Nov. 8, 2022

(54) OPTICAL COHERENCE TOMOGRAPHY RECEIVER

(71) Applicant: Alcon Inc., Fribourg (CH)

(72) Inventors: Muhammad K Al-Qaisi, Ladera Ranch, CA (US); Tomas Sedlacek, Framingham, MA (US); Joseph T. Traynor, North Berwick, ME (US); Antonije M. Radojevic, Belmont, MA (US); Todd Schernig, North Billerica, MA (US); Sahar Hosseinzadeh Kassani, Lake Forest, CA (US)

(73) Assignee: Alcon Inc., Fribourg (CH)

( * ) Notice: Subject to any disclaimer, the term of this patent is extended or adjusted under 35 U.S.C. 154(b) by 532 days.

(21) Appl. No.: 16/691,697

(22) Filed: Nov. 22, 2019

(65) Prior Publication Data

US 2020/0163546 A1 May 28, 2020

Related U.S. Application Data (60) Provisional application No. 62/772,325, filed on Nov. 28, 2018.

(51) Int. Cl.
*G01B 9/02* (2022.01)
*A61B 3/10* (2006.01)
*G01B 9/02015* (2022.01)

(52) U.S. Cl.
CPC .......... *A61B 3/102* (2013.01); *G01B 9/02015* (2013.01); *G01B 9/02049* (2013.01); *G01B 9/02051* (2013.01); *G01B 2290/70* (2013.01)

(58) Field of Classification Search
CPC ................ A61B 3/102; G01B 9/02015; G01B 9/02049; G01B 9/02051; G01B 2290/70
See application file for complete search history.

(56) References Cited

U.S. PATENT DOCUMENTS

| | | | | |
|---|---|---|---|---|
| 2007/0285669 | A1* | 12/2007 | Ajgaonkar | ........... A61B 5/0059 356/482 |
| 2009/0116034 | A1* | 5/2009 | Takahashi | .......... G01B 9/02081 356/498 |
| 2013/0215730 | A1 | 8/2013 | Okamoto | |
| 2014/0139842 | A1* | 5/2014 | Rhoadarmer | ...... G01B 9/02081 356/477 |

FOREIGN PATENT DOCUMENTS

| EP | 2957218 A1 | 12/2015 |
|---|---|---|
| JP | H03-155519 A | 7/1991 |

OTHER PUBLICATIONS

Bouma et al., "Fourier-domain optical coherence tomography: recent advances toward clinical utility", Mar. 4, 2009, pp. 111-118, vol. 20, No. 1, Current Opinion in Biotechnology.

(Continued)

*Primary Examiner* — Jonathan M Hansen (57) ABSTRACT

An Optical Coherence Tomography receiver may include prisms, polarizing beam splitters, reflectors, lenses, and a photodetector array arranged in a compact package. Sample and reference beams are combined into an interference beam and split in two. The two resulting interference beams are then split into two polarization sates each. The optical path lengths for both pairs of interference beams with the same polarization state are equal or nearly equal.

22 Claims, 6 Drawing Sheets

(56) References Cited

OTHER PUBLICATIONS

THORLABS. "Operation Manual—Thorlabs Instrumentation—Balanced polarization diversity detector for PS-OCT." Apr. 5, 2019.
THORLABS. "Polarization Balanced Detector [online]." [Retrieved Nov. 16, 2019.] Retrieved from https://www.thorlabs.com/newgrouppage9.cfm?objectgroup_id=4027&pn=INT-POL-1300.
Wang et al., "Silicon photonic integrated circuit swept-source optical coherence tomography receiver with dual polarization, dual balanced, in-phase and quadrature detection", Jul. 1, 2015, pp. 2562-2574, vol. 6, No. 7, Biomedical Optics Express.

* cited by examiner

OPTICAL COHERENCE TOMOGRAPHY RECEIVER

TECHNICAL FIELD

Embodiments disclosed herein are related to devices, systems, and methods for Optical Coherence Tomography (OCT).

BACKGROUND

Current ophthalmic refractive surgical methods, such as cataract surgery, intra-corneal inlays, laser-assisted in situ keratomileusis (LASIK), and photorefractive keratectomy (PRK), rely on ocular biometry data to prescribe the best refractive correction. Historically, ophthalmic surgical procedures used ultrasonic biometry instruments to image portions of the eye. In some cases, these biometric instruments generated a so-called A-scan of the eye: an acoustic echo signal from all interfaces along an imaging axis that was typically aligned with an optical axis of the eye: either parallel with it, or making only a small angle. Other instruments generated a so-called B-scan, essentially assembling a collection of A-scans, taken successively as a head or tip of the biometry instrument was scanned along a scanning line. This scanning line was typically lateral to the optical axis of the eye. These ultrasonic A-scans or B-scans were then used to measure and determine biometry data, such as an ocular axial length, an anterior depth of the eye, or the radii of corneal curvature.

In some surgical procedures, a second, separate keratometer was used to measure refractive properties and data of the cornea. The ultrasonic measurements and the refractive data were then combined in a semi-empirical formula to calculate the characteristics of the optimal intra-ocular lens (IOL) to be prescribed and inserted during the subsequent cataract surgery.

More recently, ultrasonic biometry devices have been rapidly giving way to optical imaging and biometry instruments that are built on the principle of Optical Coherence Tomography (OCT). OCT is a technique that enables micron-scale, high-resolution, cross-sectional imaging of the human retina, cornea, lens or other eye structure. Optical waves are reflected from an object or sample and a computer produces images of cross sections or three-dimensional volume renderings of the sample by using information on how the waves are changed upon reflection.

OCT may be performed based on time-domain processing or Fourier-domain processing. The latter approach includes a technique known as swept-source OCT, where the spectral components of the optical signal used to illuminate the sample are encoded in time. In other words, the optical source is swept (or stepped) across an optical bandwidth, with the interference signal produced by the combination of the source signal and the reflected signal being sampled at several points across this optical bandwidth. A receiver receives the source signal (also called the reference signal or the signal that traverses the reference arm) and the sample signal (the signal reflected from the sample) and produces the interference signal. The interference signal (that is the interference pattern when the reference and sample signals are combined or interfere with each other) is then directed to a detector.

OCT technology is now commonly used in clinical practice, with such OCT instruments are now used in 80-90% of all IOL prescription cases. Among other reasons, their success is due to the non-contact nature of the imaging and to the higher precision than that of the ultrasound biometers.

Even with these recent advances, however, substantial further growth and development is needed for the functionalities and performance of biometric and imaging instruments.

SUMMARY

In one example, an Optical Coherence Tomography (OCT) receiver receives a sample beam and a reference beam and combines the sample beam and the reference beam into an interference beam. The OCT receiver comprises first and second prisms aligned with each other, with two faces in contact and having a beam splitting non-polarizing interface in-between. The first prism is arranged to receive one of the sample beam or the reference beam, and the second prism is arranged to receive the other of the sample beam or the reference beam. The interference beam is created and split into a first interference beam and a second interference beam at the non-polarizing contact interface between the first and second prism. First and second polarizing beam splitters are aligned with each other. The first and second polarizing beam splitters are arranged adjacent to the first prism. The first and second polarizing beam splitters are arranged to split the first interference beam into first and second polarization states. A delay path is arranged adjacent to the second prism. The delay path is configured to receive the second interference beam. Third and fourth polarizing beam splitters are arranged adjacent to each other. The third and fourth polarizing beam splitters are arranged adjacent to the delay path. The third and fourth polarizing beam splitters are arranged to split the second interference beam into first and second polarization states. A photodetector array is configured to receive the first polarization state of the first interference beam, the second polarization state of the first interference beam, the first polarization state of the second interference beam, and the second polarization state of the second interference beam.

The OCT receiver may also comprise a first collimating lens arranged to receive one of the sample beam or reference beam and collimate and direct the one of the sample beam or reference beam to the first prism; and a second collimating lens arranged to receive the other of the sample beam or reference beam and direct the other of the sample beam or reference beam to the second prism.

The OCT receiver may also comprise four lenses: a first lens arranged to receive the first polarization state of the first interference beam; a second lens arranged to receive the second polarization state of the first interference beam; a third lens arranged to receive the first polarization state of the second interference beam; and a fourth lens arranged to receive the second polarization state of the second interference beam. In some cases, these lenses may be ball lenses.

In some cases, the delay path may be a prism, the prism having first and second faces, the first face of the prism adjacent to the second prism, and the second face of the prism adjacent to the third and fourth polarizing beam splitters. In other cases, the delay path may be a pair of reflectors located between the second prism and the third and fourth polarizing beam splitters.

A first optical path length from the adjacent faces (or non-polarizing contact interface) of the first and second non-polarizing splitters (which may be a prism) to a first photodetector of the photodetector array that receives the first polarization state of the first interference beam is equal or nearly equal to a second optical path length from the adjacent faces (or non-polarizing contact interface) of the first and second non-polarizing splitters (which may be a prism) to a second photodetector of the photodetector array that receives the first polarization state of the second interference beam.

A third optical path length from the adjacent faces (or non-polarizing contact interface) of the first and second non-polarizing splitters (which may be a prism) to a third photodetector of the photodetector array that receives the second polarization state of the first interference beam is equal or nearly equal to a fourth optical path length from the adjacent faces (or non-polarizing interface) of the first and second non-polarizing splitters (which may be a prism) to a fourth photodetector of the photodetector array that receives the second polarization state of the second interference beam.

In some cases, the first and second prisms, the delay path, and the first, second, third, and fourth polarizing beam splitters comprise a single assembly wherein the first and second prisms, the delay path, and the first, second, third, and fourth polarizing beam splitters comprise a single assembly. The single assembly is tilted by an angle of between one and five degrees from a horizontal plane containing the sample beam and the reference beam. An angle of incidence of the both the sample beam and the reference beam on the first face of the first prism and the first face of the second prism is between one and five degrees.

In some cases, the two beam collimating lenses, the first and second prisms, the delay path, the first, second, third, and fourth polarizing beam splitters, the four lenses in front of the detector array, and the detector array, comprise a single assembly that forms a compact package with a volume of less than 23 millimeters by 37 millimeters by 10 millimeters.

In another example, an Optical Coherence Tomography (OCT) receiver receives a sample beam and a reference beam and combines the sample beam and reference beam into an interference beam. The OCT receiver comprises an assembly comprising a non-polarizing beam splitter prism, a first reflector, and a second reflector. The first and second reflectors are arranged on opposite sides of the prism. The prism is arranged to receive one of the sample beam or the reference beam, and the second reflector is arranged to receive the other of the sample beam or the reference beam. The interference beam is created and split into a first interference beam and a second interference beam in the prism. First and second polarizing beam splitters are aligned with each other. The first and second polarizing beam splitters are arranged adjacent to the first reflector. The first and second polarizing beam splitters are arranged to split the first interference beam into first and second polarization states. A delay path is arranged adjacent to the non-polarizing beam splitter prism and second reflector. The delay path is configured to receive the second interference beam. Third and fourth polarizing beam splitters are arranged adjacent to each other. The third and fourth polarizing beam splitters are arranged adjacent to the delay path. The third and fourth polarizing beam splitters are arranged to split the second interference beam into first and second polarization states. A photodetector array is configured to receive the first polarization state of the first interference beam, the second polarization state of the first interference beam, the first polarization state of the second interference beam, and the second polarization state of the second interference beam.

The OCT receiver may also comprise a first collimating lens arranged to receive one of the sample beam or reference beam and direct the one of the sample beam or reference beam to the prism; and a second collimating lens arranged to receive the other of the sample beam or reference beam and direct the other of the sample beam or reference beam to the second reflector.

The OCT receiver may also comprise four lenses: a first lens arranged to receive the first polarization state of the first interference beam; a second lens arranged to receive the second polarization state of the first interference beam; a third lens arranged to receive the first polarization state of the second interference beam; and a fourth lens arranged to receive the second polarization state of the second interference beam. These lenses may all be ball lenses.

In some cases, the delay path comprises a prism having first and second faces. The first face of the prism is adjacent to the non-polarizing beam splitter prism, and the second face of the prism is adjacent to the third and fourth polarizing beam splitters. In other cases, the delay path may be a pair of reflectors located between the prism and the third and fourth polarizing beam splitters.

A first optical path length from the non-polarizing splitter interface to a first photodetector of the photodetector array that receives the first polarization state of the first interference beam is equal or nearly equal to a second optical path length from the non-polarizing splitter interface to a second photodetector of the photodetector array that receives the first polarization state of the second interference beam.

A third optical path length from the non-polarizing splitter to a third photodetector of the photodetector array that receives the second polarization state of the first interference beam is equal or nearly equal to a fourth optical path length from the non-polarizing splitter to a fourth photodetector of the photodetector array that receives the second polarization state of the second interference beam.

The first and second reflector, the non-polarizing beam splitter prism, the delay path, and the first, second, third, and fourth polarizing beam splitters comprise a single assembly located in a plane. The plane is tilted by an angle of between one and five degrees from a horizontal plane containing the sample beam and the reference beam.

The first and second reflectors, the non-polarizing beam splitter prism, the delay path, and the first, second, third, and fourth polarizing beam splitters comprise a single assembly that forms a compact package with a volume of less than 23 millimeters by 37 millimeters by 10 millimeters.

The embodiments described herein may be used to provide and/or operate an all-in-one device to achieve optimized OCT performance for each of several different application modes. Other advantages and variations of the above-summarized embodiments are described below.

DETAILED DESCRIPTION

In the following description, specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

Figure 1:
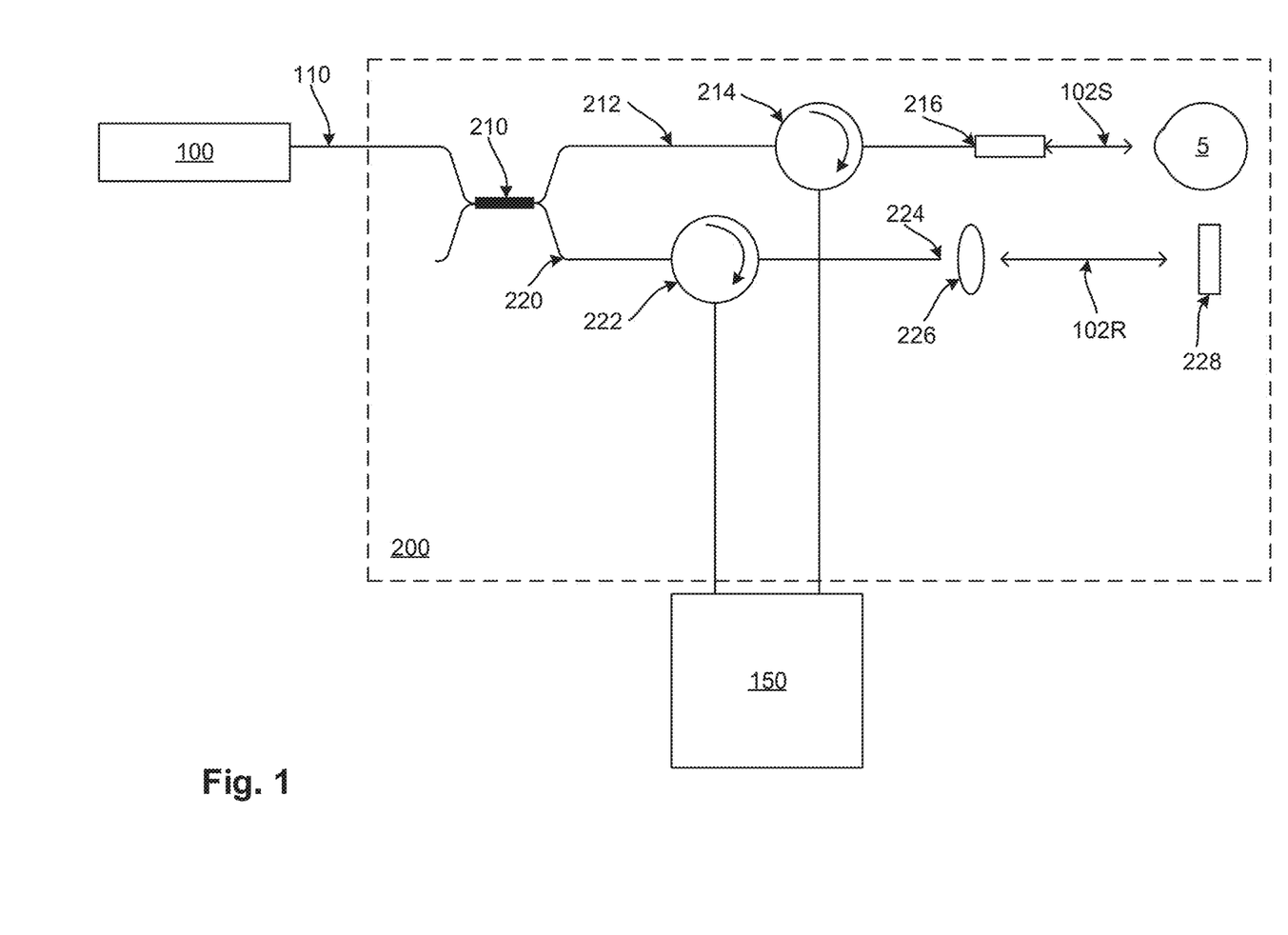
FIG. 1 illustrates components of an example swept-source Optical Coherence Tomography (OCT) system.

FIG. 1 illustrates an example SSOCT system 10, which comprises a swept optical source 100, an interferometer subsystem 200, and a detector receiver 150. It will be appreciated that the details shown here are an example only; other systems may vary in well-known ways.

Swept optical source 100 is typically designed for wavelength tuning, to generate swept optical signals that repeatedly scan over a predetermined optical tuning range, e.g., over an optical wavelength range of 100 nm or greater, at a scanning repetition rate of 1 kilohertz (kHz) or greater. The bandwidth of the optical emission, i.e., the full-width half-maximum (FWHM) bandwidth is typically less than 10 GHz. Interferometer subsystem 200, in this particular example implemented as a Mach-Zehnder-type interferometer designed for operation at, for example, central wavelengths around 1060 nm, and receiver 150, are used to analyze the optical signals reflected from the imaged object 5, which may be a human eye. It will be appreciated that interferometer subsystem 200 may be based on a different design when designed for different wavelengths. Other central wavelengths may include those around 1310 nm or 850 nm.

As seen in FIG. 1, the swept optical output from the swept optical source 100 is coupled to an optical fiber coupler 210 in interferometer subsystem, via optical fiber 110. Optical fiber coupler 210 may be a 90/10 optical fiber coupler, for example. The swept optical signal is divided by the coupler 210 between a reference arm 220 and a sample arm 212.

The optical fiber of the reference arm 220 terminates at a fiber end-face 224. The light 102R exiting from the reference arm fiber endface 224 is collimated by a lens 226 and reflected by a mirror 228, in the illustrated implementation. Mirror 228 has an adjustable fiber-to-mirror distance, in one example. This distance determines a reference point in the depth range being imaged, i.e., the position in the sample 5 of the zero-path length difference between the reference arm 220 and the sample arm 212. This distance may be adjusted, in some embodiments, for different sampling probes and/or imaged samples. Light returning from the reference mirror 228 is returned to a reference arm circulator 222 and directed to receiver 150.

The fiber on sample arm 212 terminates at the sample arm probe 216. The exiting swept optical signal 102S is focused by the probe 216 onto the sample 5. Light returning from the sample 5 is returned to a sample arm circulator 214 and directed to the receiver 150. The reference arm signal and the sample arm signal are combined in the receiver 150 to generate an optical interference signal as more clearly described below.

In this context, the sample beam is the light beam reflected from the sample, and the reference beam is the light beam reflected from the mirror in the reference arm. The sample beam is associated with the sample arm, and the reference beam is associated with the reference arm. In an example interferometer, the light source (in some cases a swept optical source or swept source laser) produces a beam of light at a central wavelength (in some cases a central wavelength of 1060 nm). The beam of light is then split into two beams—one of which is directed at the sample (the sample arm), the other of which is directed at the reference path (the reference arm). The optical paths of the reference arm and the sample arm are generally of similar lengths. The sample beam and the reference beam are combined to produce an interference beam.

Figure 2:
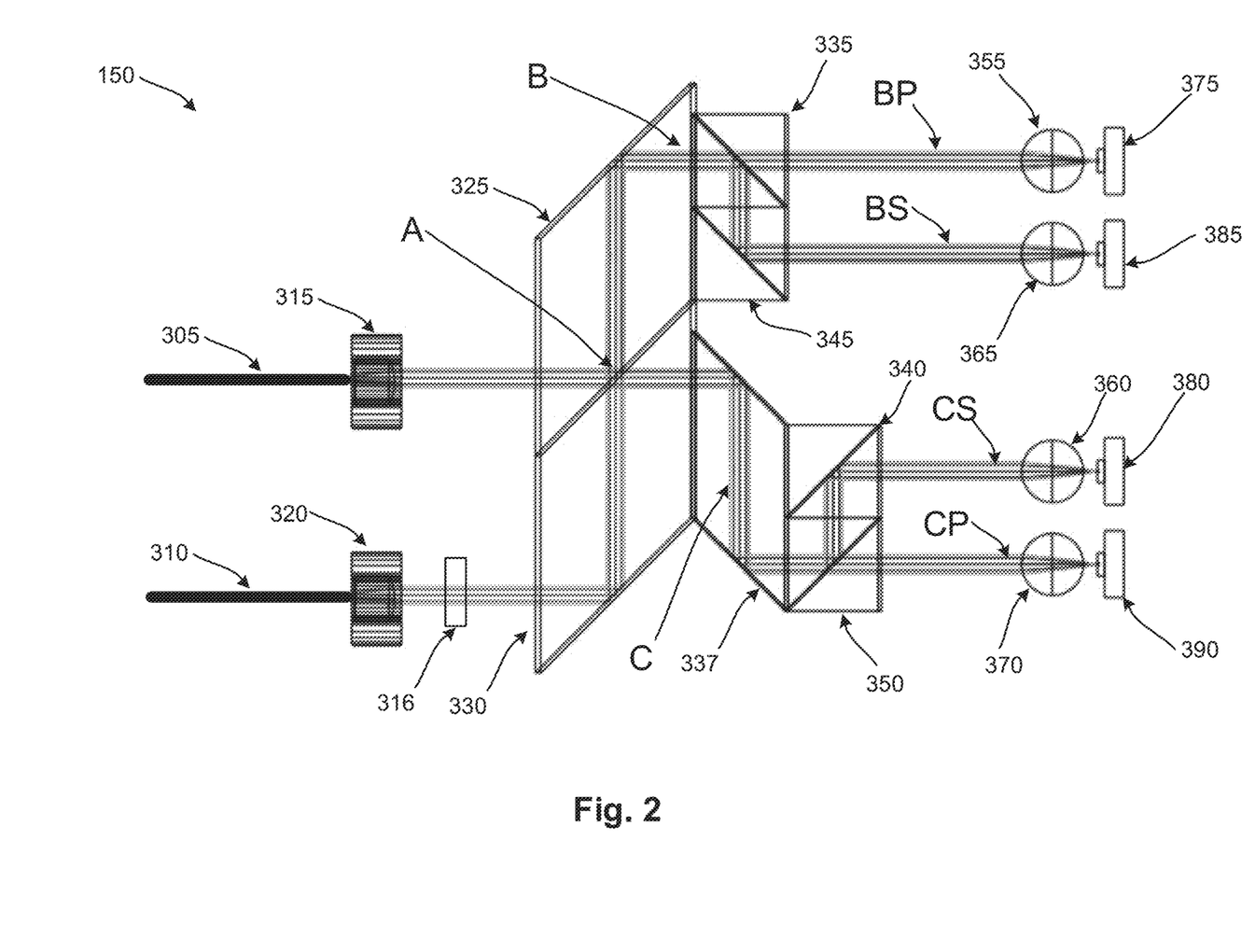
FIG. 2 illustrates an example of an OCT receiver in a top view.

FIG. 2 shows an example of an OCT detector (or OCT receiver in a top view). In FIG. 2, a sample beam 305 is reflected from the sample 5. A reference beam 310 returns from the reference arm. Sample beam 305 passes through collimating lens 315. Reference beam 310 passes through collimating lens 320 and polarizer 316. Collimated sample beam 305 then enters prism 325, and the collimated reference beam 310 enters prism 330. Collimated sample beam 305 is reflected from a surface (or non-polarizing beam splitting contact interface) of prisms 325 and 330, and the collimated reference beam 310 is reflected from a surface of prism 330 as shown in FIG. 2. Interference between the sample beam 305 and the reference beam 310 occurs at point A where prism 325 and prism 330 meet. The interference beam is split into two beams, B and C, by prism 325 and prism 330. Beam B enters polarizing beam splitter (PBS) 335 where it is split into two beams BP and BS. Beam BP exits PBS 335 and enters lens 355 where it is focused onto photodetector 375. Beam BS exits PBS 335, is reflected by reflector 345, and enters lens 365 where it is focused onto photodetector 385. In a similar manner, beam C is also split into beam CP and CS. Beam C exits prism 330 and enters a delay path 337. In this example, delay path 337 comprises a prism with a pair of opposite facets acting as reflectors aligned to direct beam C into PBS 350. Beam C enters polarizing beamsplitter (PBS) 350 where it is split into two beams CP and CS. Beam CP exits PBS 350 and enters lens 370 where it is focused onto photodetector 390. Beam CS exits PBS 350, is reflected by reflector 340, and enters lens 360 where it is focused onto photodetector 380.

Structurally, the example OCT receiver of FIG. 2 comprises a pair of collimating lenses 315 and 320 aligned with a pair of prisms 325 and 330 so as to produce an interference of the sample beam 305 and the reference beam 310 at point A. A polarizer 316 is in the optical path of the reference arm between collimating lens 320 and NPBS/prism 330. The interference beam is split into two beams B and C. Prism 325 is aligned with PBS 335 so as to split the interference beam B into two polarization states (beams BP and BS). A reflector 345 is aligned with PBS 335 to direct the beam BS to lens 365. Lens 365 is aligned with photodetector 385. PBS 335 is aligned with lens 355 to direct the beam BP onto photodetector 375. In a similar manner, prism 330 is aligned with delay path 337. Delay path 337 is aligned with PBS 350 so as to split the interference beam C into two polarization states (beams CP and CS). A reflector 340 is aligned with PBS 350 to direct the beam CS to lens 360. Lens 360 is aligned with photodetector 380. PBS 350 is aligned with lens 370 to direct the beam CP onto photodetector 390.

Functionally, the example OCT receiver of FIG. 2 receives sample beam 305 and reference beam 310, causes the two beams to interfere with each other so as to produce an interference pattern, splits the interference beam into two beams B and C. The two beams B and C take two parallel optical paths and are further split into two polarization states. Each of the two polarization states (BP, BS and CP, CS) for each of the two beams (B and C) are then directed to an array of photodetectors (375, 385, 390, and 380). The optical path length of the first polarization state BP from the non-polarizing interface A up to its detector 375 is close-to-equal to the optical path of the first polarization state CP from the non-polarizing interface A up to its detector 390. The optical path length of the second polarization state BS from the non-polarizing interface A up to its detector 385 is close-to-equal to the optical path of the second polarization state CS from the non-polarizing interface A up to its detector 380.

Prisms 325 and 300 are coupled together along a surface to form a non-polarizing beam splitter (NPBS). In this example, prisms 325 and 330 are attached rhomboid prisms with a non-polarizing beam-splitting coating at their interface. The adjacent surfaces of prisms 325 and 330 form an NPBS. Sample beam 305 and reference beam 310 are aligned to enter the NPBS such that they are each 50/50 power-split and simultaneously combined by the NPBS non-polarizing interface. Two spatially separated, orthogonal interference beams are created, each one carrying 50% of the sample beam and 50% of the reference beam. A first face of prism 325 is adjacent to a first face of prism 330. The interference beam is created and split into a first interference beam and a second interference beam where the first face of the first prism and the first face of the second prism meet.

In the example of FIG. 2, collimating lenses 315 and 320 may be any type of lens or optical element that collimates a light beam. Other types of lenses may also be used in place of collimating lenses 315 and 320. In another example of OCT receiver, collimating lenses 315 and 320 may be absent. Sample beam 301 and reference beam 310 may be directed to prism 325 and prism 330, respectively without passing through collimating lenses or other optical elements inside the OCT receiver. In the example of FIG. 2, collimating lenses 315 and 320 are a matched pair of lenses or lenses of the same type. In one example, collimating lenses 315 and 320 have an effective focal length (EFL) of 1.8 mm and collimate a beam with a diameter between 300 micrometers and 700 micrometers.

In the example OCT receiver of FIG. 2, prisms 325 and 330 may be implemented by rhomboid prisms, cubic prisms, rectangular prisms, or prisms of other shapes. Instead of prisms, other types of optical elements suitable for the example OCT receiver of FIG. 2 include plate beam splitters, cube beam splitters, or the like. Functionally, prism 325 and prism 330 together facilitate the interference of a sample beam and a reference beam as well as splitting the interference beam into two interference beams. In the example of FIG. 2, the interface between adjacent surfaces of prisms 325 and 330 (at point A) act as a non-polarizing beam splitter.

In the example OCT receiver of FIG. 2, PBS 335 and 350 are beam splitters, and may be implemented by prisms, including cubic prisms, rectangular prisms, or prisms of other shapes. Other types of PBS suitable for the example OCT receiver of FIG. 2 include plate beam splitters, cube beam splitters, or the like. Functionally, PBS 335 and PBS 350 both split the interference beam into two interference beams with different polarization states (generally denoted as polarization states P and S). In this case, the polarization states are orthogonal to each other. In the example of FIG. 2, PBS 335 and PBS 350 are a matched pair of beam splitters or beam splitters of the same type.

In the example OCT receiver of FIG. 2, reflectors 340 and 345 may be implemented by mirrors, including mirrors designed to reflect light of certain wavelengths. In other examples, reflectors 340 and 345 may be implemented with prisms or beam splitters of various types. For example, reflectors 340 and 345 may be implemented with a surface of a prism or beam splitter. In FIG. 2, reflectors 40 and 345 have the same form factor as PBS 335 and PBS 350. This form factor allows for a compact design of receiver 150.

In the example OCT receiver of FIG. 2, lenses 355, 360, 365, and 370 may be implemented with lens element to collimate, focus or otherwise alter the optical path of a light beam. Numerous types of lenses may be used to direct the light beams to photodetectors 375, 380, 385, and 390. In one example, a 2.0 mm BK7 ball lens is used for each of the lenses 355, 360, 365, and 370 in order to focus the light beams into a spot size of approximately 75 micrometers.

In the example OCT receiver of FIG. 2, delay path 337 introduces a delay in the path of interference beam C to compensate for the longer optical path of interference beam B. In other words, delay path 337 introduces an optical path length so that the optical path from collimating lens 315 or point (interface) A to photodetector 375 is equal or nearly equal to the optical path from collimating lens 320 or point (interface) A to photodetector 390. Likewise, delay path 337 introduces an optical path length so that the optical path from collimating lens 315 or point (interface) A to photodetector 385 is equal or nearly equal to the optical path from collimating lens 320 or point (interface) A to photodetector 380. Delay path 337 may be implemented using a pair of mirrors, a beam splitter, a prism, or other optical element designed to introduce a delay or extra length in an optical path.

In the example OCT receiver of FIG. 2, photodetectors 375, 380, 385, and 390 receive polarized light beams BP, CS, BS, and CP. Typically, photodetectors 375, 380, 385, and 390 are semiconductor devices that convert photons into electric current. In this case, photodetectors 375, 380, 385, and 390 may be polarization sensitive elements.

Figure 3:
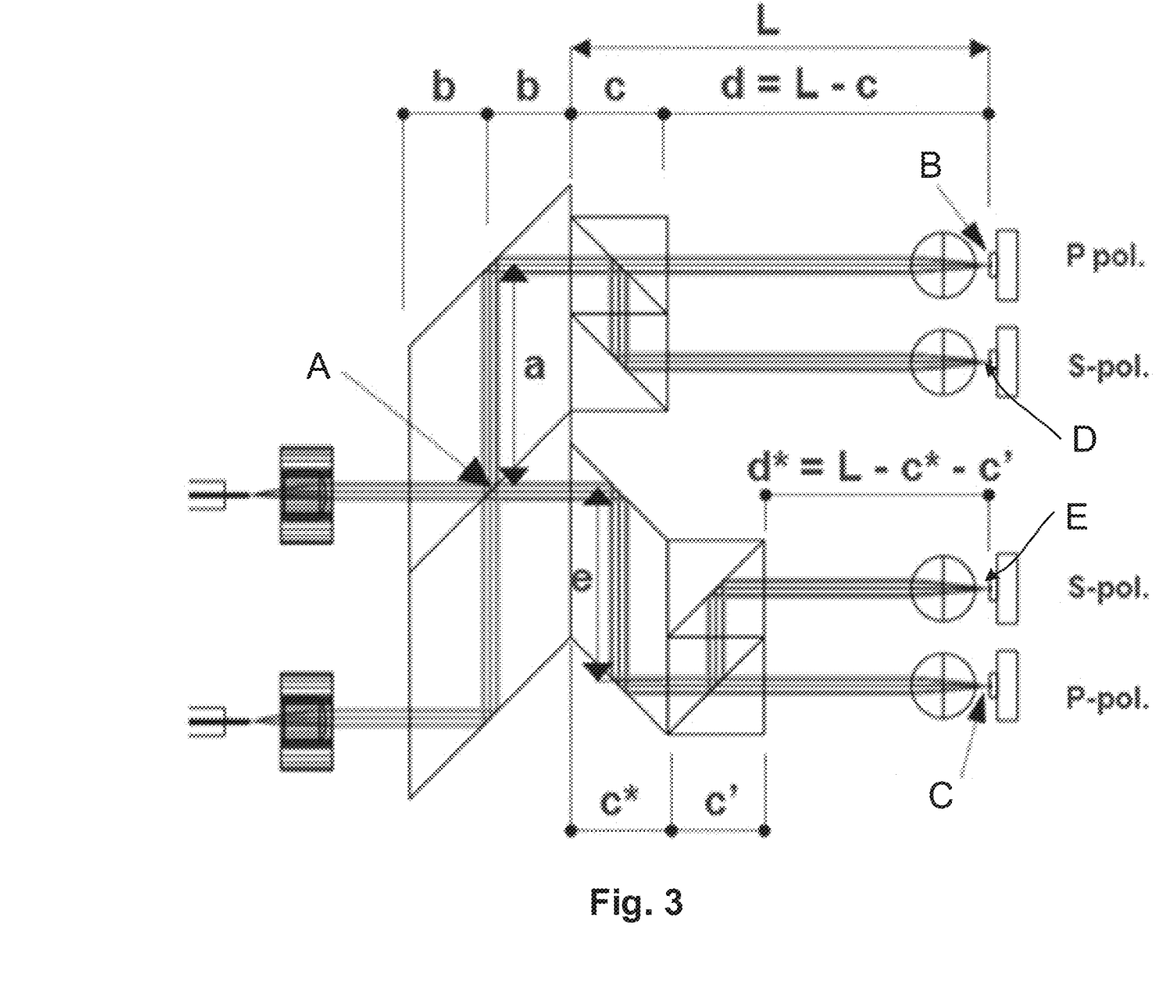
FIG. 3 depicts optical path lengths of the example OCT receiver of FIG. 2.

FIG. 3 depicts optical path lengths of the example OCT receiver of FIG. 2. In the example of FIG. 3, The optical path length from A to B equals or nearly equals the optical path length from A to C, and the optical path length from A to D equals or nearly equals the optical path length from A to E. In this example, the optical glass used in the optical paths shown in FIG. 3 is BK7 glass with a refractive index of approximately 1.5067 at 1060 nm. For purposes of showing the optical path lengths, in FIG. 3, c=c*=c' and the other path lengths are as follows:

| Optical Path Length from A to B | | |
|---|---|---|
| Path | Path length (mm) | Optical Path Length (mm) |
| a | 7 | 10.547 |
| b | 2.5 | 3.767 |
| c | 3 | 4.52 |
| L | 13 | Fixed by assembly |
| d = L − c | 10 | 10 |
| Total | | 28.834 |

And for the path A to C,

| Optical Path Length from A to C | | |
|---|---|---|
| Path | Path length (mm) | Optical Path Length (mm) |
| b | 2.5 | 3.767 |
| e | 5.99 | 9.025 |
| c' | 3 | 4.52 |
| c* | 3 | 4.52 |
| d* = L − c* − c' | 7 | 7 |
| Total | | 28.832 |

In this case, in order to ensure equal path lengths, the optical components such as NPBS and PBS are selected from the same manufacturing lots or are presorted and matched to minimize path length differences introduced by variations in optical components.

The example OCT receiver shown in FIGS. 2 and 3 provide a compact, stable package that may be used in an interferometer. With the dimensions given above, a compact package containing all of the elements occupies a volume of less than 23 mm×37 mm×10 mm. In addition, the use of lens elements, NPBS elements, and PBS elements with the geometric shapes described and shown in the Figures allow for compact assembly. This compact assembly provides optical stability as well as a physically small package that may be incorporated into a portable OCT instrument. In the example of FIG. 2, prism 325 and prism 330 may each be implemented with a rhomboid prism, PBS 335, PBS 340, PBS 345, and PBS 350 can each be implemented with cubic beam splitters, and delay path 337 may be implemented with a prism. These geometric components may be assembled and aligned into a small and stable package. As shown in FIGS. 2 and 3, the prisms 325 and 330, PBS 340, 345, 350, 355, and delay path 337 may be arranged adjacent to each other. Since the prisms, PBS, and delay path are each geometric elements (e.g., prisms) in this example, the faces of these elements may be placed adjacent to one another as shown to form a stable assembly. Moreover, the location of the lenses 355, 360, 365, 370 and photodetectors 375, 380, 385, 390 may be fixed in relation to the other elements in a single compact package.

Figure 4A:
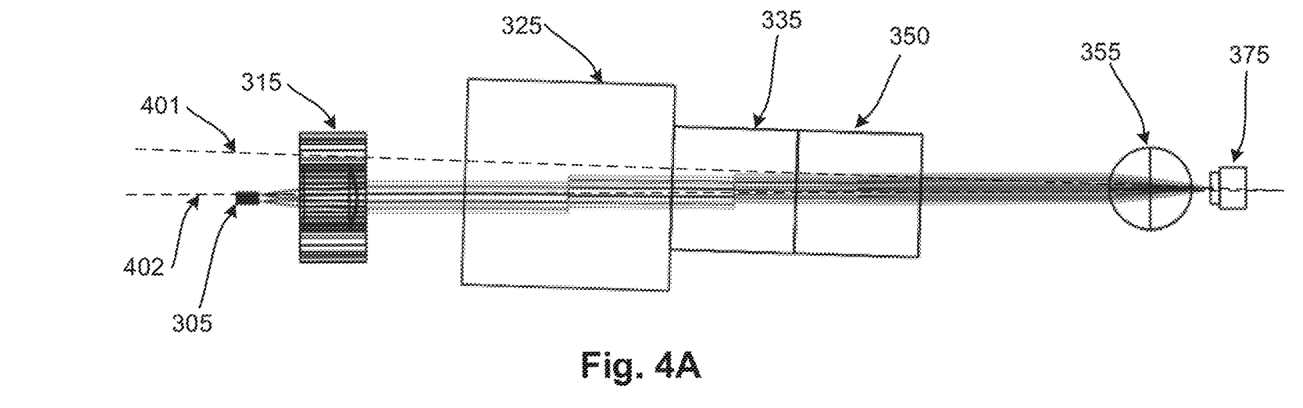
FIGS. 4A and 4B are side views of the OCT receiver of FIG. 2.
Figure 4B:
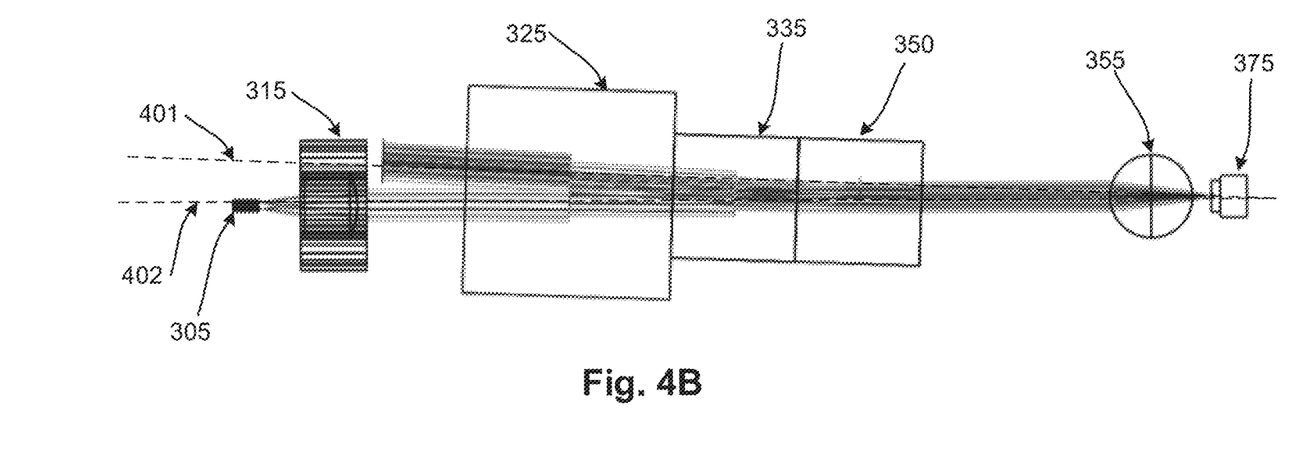

FIGS. 4A and 4B are side views of the OCT receiver of the example of FIG. 2. In FIGS. 4A and 4B, sample beam 305, collimating lens 315, prism 325, prism 335, PBS 350, lens 355 and photodetector 375 are depicted. Behind collimating lens 315 is collimating lens 320. Behind prism 325 is prism 330. Behind PBS 335 is delay path 337. Behind lens 355 are lenses 365, 360, and 370. Behind photodetector 375 are photodetectors 385, 380, and 390. A polarizer 316 may also be located in the reference path between collimating lens 320 and prism 330.

Polarizer 316 may be located at a 45 degree angle in the reference path (or optical path of the reference arm) as shown in the example of FIG. 3. In such a case, polarizer 316 will ensure proper signal matching of the P and S channels and that the P and S channels will have equal or approximately equal power. Polarizer 316 may be oriented such that proper signal matching of the P and S channels occurs—or that the P and S channels have equal or approximately equal power. In this case, light in the reference arm passes through polarizer before being split into P and S polarization. In this manner the light in the reference arm is polarized or aligned before being further split into the two polarization states (P and S).

FIGS. 4A and 4B show a tilt introduced to the optical components of the OCT receiver 150. If FIG. 2 depicts the horizontal plane of OCT receiver 150 top view, then FIGS. 4A and 4B depict the vertical plane of OCT receiver 150 side view. A tilt of approximately two degrees from the horizontal plane 402 is introduced to the assembly comprising the prisms 325 and 330, the delay path 337, and the polarizing beam splitters 335, 340, 345, 350. The tilt angle effectively becomes the angle of incidence for the horizontally directed sample beam 305 and reference beam 310 at the input surface/facet of the NPBS (i.e. the adjacent sides of prisms 325 and 330). The tilt angle is shown in FIGS. 4A and 4B as the angle between planes 401 and 402. In this example, plane 402 is the plane containing the sample beam and the reference beam. The assembly comprising the prisms 325 and 330, the delay path 337, and the polarizing beam splitters 335, 340, 345, 350 is tilted by an angle with respect to plane 402. The tilt introduced in the vertical plane of OCT receiver 150 may be in the range of one degree to five degrees, with a tilt of approximately two degrees shown in the example of FIGS. 4A and 4B (the angle between planes 401 and 402). FIG. 4A depicts the forward beams, and FIG. 4B depicts the forward and the retro-reflected beams. In order to eliminate ghosting in the system, the retro-reflected beams return at such an angle as not to pass back through collimating lenses. It has been found that a tilt of two degrees is sufficient to eliminate double retro-path interference due to the geometric separation from the forward beam.

Figure 5:
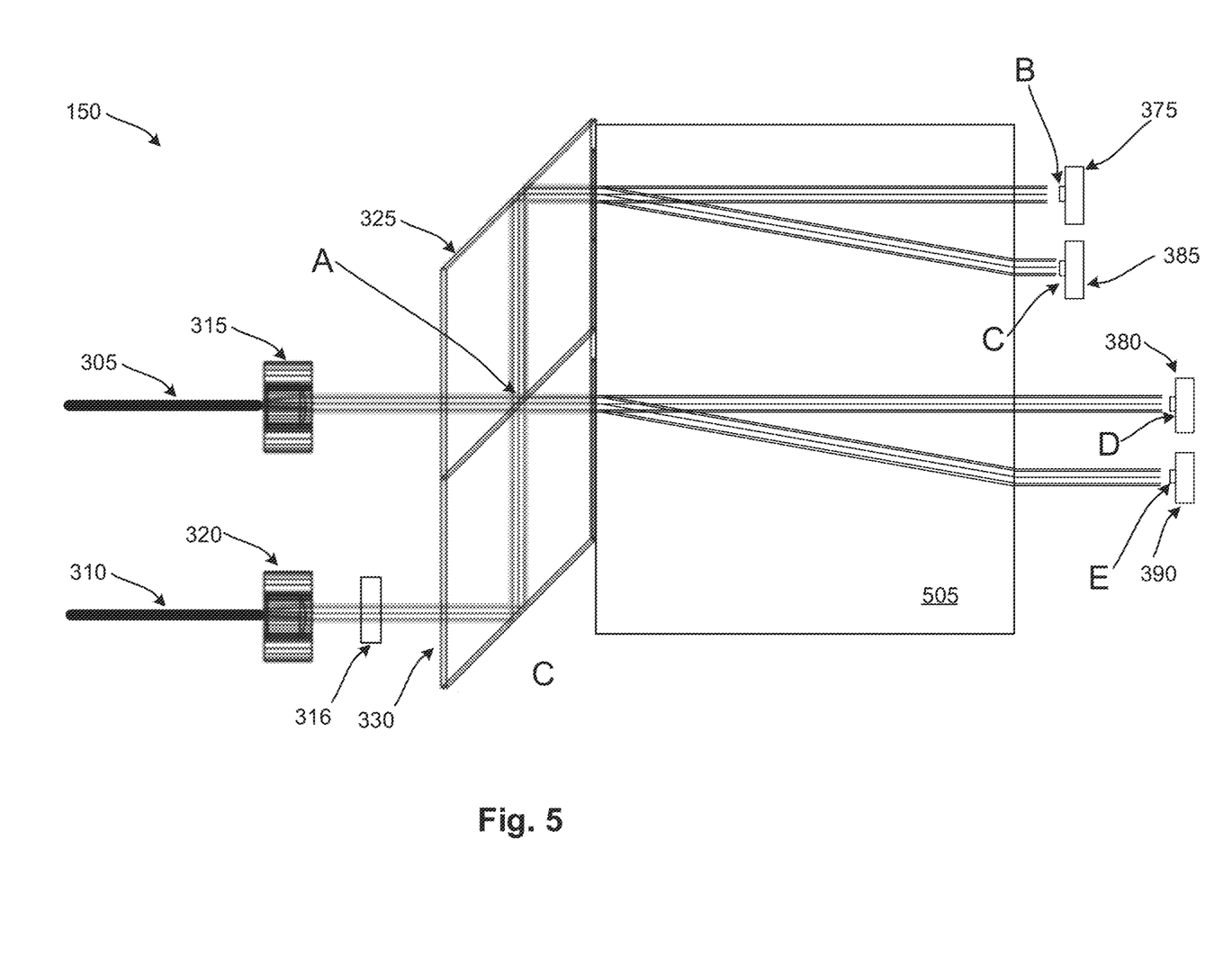
FIG. 5 illustrates an example of an OCT receiver.

FIG. 5 shows another example of an OCT receiver. In FIG. 5, a birefringent crystal 505 is used instead of PBS 335, mirror 345, delay path 337, PBS 350, and mirror 340. Lenses 355, 360, 365, and 370 are omitted for simplicity. In FIG. 5, the location of photodetectors 375, 380, 385, and 390 may be adjusted so that the optical paths from A to B and A to D are equal or nearly equal and the optical paths from A to C and A to E are equal or nearly equal.

Figure 6:
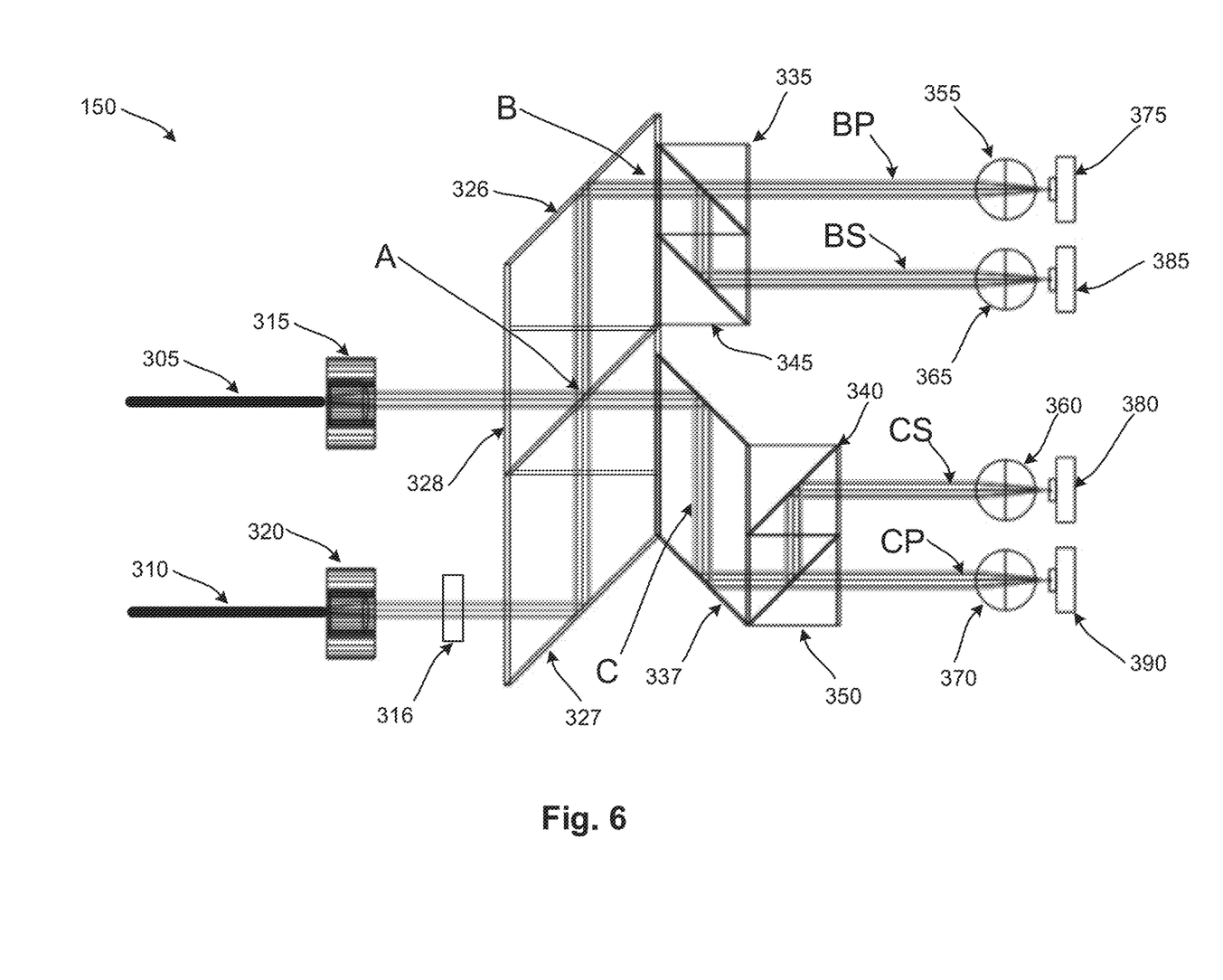
FIG. 6 illustrates an example of an OCT receiver.

FIG. 6 shows an example of an OCT receiver. In FIG. 6, NPBS 328, reflector 326, and reflector 327 replaces PRISM 325 and PRISM 330 in FIG. 2. In FIG. 6, a sample beam 305 is reflected from the sample 5. A reference beam 310 returns from the reference arm. Sample beam 305 passes through collimating lens 315. Reference beam 310 passes through collimating lens 320 and polarizer 316. Collimated sample beam 305 is reflected from reflector 326 or directed toward NPBS 328, and the collimated reference beam 310 is reflected from reflector 327 toward NPBS 328. Collimated sample beam 305 then enters NPBS 328, and the collimated reference beam 310 enters NPBS 328. Interference between the sample beam 305 and the reference beam 310 occurs at point A in NPBS 328. The interference beam is split into two beams, B and C, by NPBS 328. The remainder of the OCT receiver is the same as that depicted in FIG. 2 and described above.

Functionally, the example OCT receiver of FIG. 6 provides optical paths of the same or nearly the same lengths (i.e., matched lengths) from point A (i.e. the adjacent faces of prisms 325 and 330 or non-polarizing interface inside NPBS 328) to the photodetectors 375, and 390. It also provides optical paths of the same or nearly the same lengths (i.e., matched lengths) from point A to the photodetectors 385 and 380. The example OCT receiver of FIG. 6 receives sample beam 305 and reference beam 310, causes the two beams to interfere with each other so as to produce an interference pattern, splits the interference beam into two beams B and C. The two beams B and C take two parallel optical paths and are further split into two polarization states. Each of the two polarization states (BP, BS and CP, CS) for each of the two beams (B and C) are then directed to an array of photodetectors (375, 380, 385, 390, and 380).

It will be appreciated that the examples described provide an OCT receiver in a compact and optically stable package. The optical elements are assembled to produce matched optical paths of the same or nearly the same length.

The specific embodiments described above illustrate but do not limit the invention. It should also be understood that numerous modifications and variations are possible in accordance with the principles of the present invention, as described above and as claimed below.

What is claimed is:

1. An Optical Coherence Tomography (OCT) receiver that receives a sample beam and a reference beam and combines the sample beam and the reference beam into an interference beam, the OCT receiver comprising:

first and second prisms aligned with each other, a first face of the first prism adjacent to a first face of the second prism, the first prism arranged to receive one of the sample beam or the reference beam, and the second prism arranged to receive the other of the sample beam or the reference beam, the interference beam created and split into a first interference beam and a second interference beam where the first face of the first prism and the first face of the second prism meet;

first and second polarizing beam splitters aligned with each other, the first and second polarizing beam splitters arranged adjacent to the first prism, the first and second polarizing beam splitters arranged to split the first interference beam into first and second polarization states;

a delay path arranged adjacent to the second polarizing beam splitter, the delay path configured to receive the second interference beam;

third and fourth polarizing beam splitters arranged adjacent to each other, the third and fourth polarizing beam splitters arranged adjacent to the delay path, the third and fourth polarizing beam splitters arranged to split the second interference beam into first and second polarization states; and a photodetector array configured to receive the first polarization state of the first interference beam, the second polarization state of the first interference beam, the first polarization state of the second interference beam, and the second polarization state of the second interference beam.

2. The OCT receiver of claim 1 further comprising:
a first collimating lens arranged to receive one of the sample beam or reference beam and direct the one of the sample beam or reference beam to the first prism; and
a second collimating lens arranged to receive the other of the sample beam or reference beam and direct the other of the sample beam or reference beam to the second prism.

3. The OCT receiver of claim 1 further comprising four lenses:
a first lens arranged to receive the first polarization state of the first interference beam;
a second lens arranged to receive the second polarization state of the first interference beam;
a third lens arranged to receive the first polarization state of the second interference beam; and
a fourth lens arranged to receive the second polarization state of the second interference beam.

4. The OCT receiver of claim 3 wherein the first, second, third, and fourth lenses are each ball lenses.

5. The OCT receiver of claim 1 wherein the delay path comprises a prism, the prism having first and second faces, the first face of the prism adjacent to the second prism, and the second face of the prism adjacent to the third and fourth polarizing beam splitters.

6. The OCT receiver of claim 1 wherein the delay path comprises a pair of reflectors located between the second prism and the third and fourth polarizing beam splitters.

7. The OCT receiver of claim 1 wherein a first optical path length from the adjacent faces of the first and second prisms to a first photodetector of the photodetector array that receives the first polarization state of the first interference beam is equal or nearly equal to a second optical path length from the adjacent faces of the first and second prisms to a second photodetector of the photodetector array that receives the first polarization state of the second interference beam.

8. The OCT receiver of claim 1 wherein a third optical path length from the adjacent faces of the first and second prisms to a third photodetector of the photodetector array that receives the second polarization state of the first interference beam is equal or nearly equal to a fourth optical path length from the adjacent faces of the first and second prisms to a fourth photodetector of the photodetector array that receives the second polarization state of the second interference beam.

9. The OCT receiver of claim 1 wherein the first and second prisms, the delay path, and the first, second, third, and fourth polarizing beam splitters comprise a single assembly, the single assembly tilted by an angle of between one and five degrees from a horizontal plane containing the sample beam and the reference beam.

10. The OCT receiver of claim 1 wherein an angle of incidence of the both the sample beam and the reference beam on the first face of the first prism and the first face of the second prism is between one and five degrees.

11. The OCT receiver of claim 1 wherein, the first and second prisms, the delay path, and the first, second, third, and fourth polarizing beam splitters, comprise a single assembly that forms a compact package with a volume of less than 23 millimeters by 37 millimeters by 10 millimeters.

12. An Optical Coherence Tomography (OCT) receiver that receives a sample beam and a reference beam and combines the sample beam and reference beam into an interference beam, the OCT receiver comprising:

an assembly comprising a prism, a first reflector, and a second reflector, the first and second reflectors arranged on opposite sides of the prism, the prism arranged to receive one of the sample beam or the reference beam, and the first reflector arranged to receive the other of the sample beam or the reference beam, the interference beam created and split into a first interference beam and a second interference beam in the prism;

first and second polarizing beam splitters aligned with each other, the first and second polarizing beam splitters arranged adjacent to the first reflector, the first and second polarizing beam splitters arranged to split the first interference beam into first and second polarization states;

a delay path arranged adjacent to the non-polarizing beam splitter and second reflector, the delay path configured to receive the second interference beam;

third and fourth polarizing beam splitters arranged adjacent to each other, the third and fourth polarizing beam splitters arranged adjacent to the delay path, the third and fourth polarizing beam splitters arranged to split the second interference beam into first and second polarization states; and a photodetector array configured to receive the first polarization state of the first interference beam, the second polarization state of the first interference beam, the first polarization state of the second interference beam, and the second polarization state of the second interference beam.

13. The OCT receiver of claim 12 further comprising:
a first collimating lens arranged to receive one of the sample beam or reference beam and direct the one of the sample beam or reference beam to the prism; and a second collimating lens arranged to receive the other of the sample beam or reference beam and direct the other of the sample beam or reference beam to the second reflector.

14. The OCT receiver of claim 12 further comprising:
a first lens arranged to receive the first polarization state of the first interference beam;
a second lens arranged to receive the second polarization state of the first interference beam;
a third lens arranged to receive the first polarization state of the second interference beam; and
a fourth lens arranged to receive the second polarization state of the second interference beam.

15. The OCT receiver of claim 14 wherein the first, second, third, and fourth lenses are each ball lenses.

16. The OCT receiver of claim 12 wherein the delay path comprises a prism, the prism having first and second faces, the first face of the prism adjacent to the prism, and the second face of the prism adjacent to the third and fourth polarizing beam splitters.

17. The OCT receiver of claim 12 wherein the delay path comprises a pair of reflectors located between the prism and the third and fourth polarizing beam splitters.

18. The OCT receiver of claim 12 wherein a first optical path length from the non-polarizing splitter to a first photodetector of the photodetector array that receives the first polarization state of the first interference beam is equal or nearly equal to a second optical path length from the non-polarizing splitter to a second photodetector of the photodetector array that receives the first polarization state of the second interference beam.

19. The OCT receiver of claim 12 wherein a third optical path length from the non-polarizing splitter to a third photodetector of the photodetector array that receives the second polarization state of the first interference beam is equal or nearly equal to a fourth optical path length from the non-polarizing splitter to a fourth photodetector of the photodetector array that receives the second polarization state of the second interference beam.

20. The OCT receiver of claim 12 wherein the first and second reflector, the prism, the delay path, and the first, second, third, and fourth polarizing beam splitters comprise a single assembly tilted by an angle of between one and five degrees with respect to plane containing the sample beam and the reference beam.

21. The OCT receiver of claim 12 wherein an angle of incidence of the both the sample beam and the reference beam on the first face of the first prism and the first face of the second prism is between one and five degrees.

22. The OCT receiver of claim 12 wherein, the first and second reflectors, the prism, the delay path, and the first, second, third, and fourth polarizing beam splitters, comprise a single assembly that forms a compact package with a volume of less than 23 millimeters by 37 millimeters by 10 millimeters.

\* \* \* \* \*